United States Patent
Zühlke et al.

(10) Patent No.: US 12,031,098 B2
(45) Date of Patent: Jul. 9, 2024

(54) METHOD OF MARKING A PETROLEUM HYDROCARBON

(71) Applicant: SICPA HOLDING SA, Prilly (CH)

(72) Inventors: Martin Zühlke, Berlin (DE); Daniel Riebe, Potsdam (DE); Toralf Beitz, Potsdam (DE); Thomas Tiller, Bussigny (CH); Juan Lopez Gejo, Lausanne (CH); Ünige Laskay, St. Sulpice (CH)

(73) Assignee: SICPA HOLDING SA, Prilly (CH)

( * ) Notice: Subject to any disclaimer, the term of this patent is extended or adjusted under 35 U.S.C. 154(b) by 0 days.

(21) Appl. No.: 17/782,433

(22) PCT Filed: Nov. 26, 2020

(86) PCT No.: PCT/EP2020/083471
§ 371 (c)(1),
(2) Date: Jun. 3, 2022

(87) PCT Pub. No.: WO2021/110526
PCT Pub. Date: Jun. 10, 2021

(65) Prior Publication Data
US 2023/0029106 A1 Jan. 26, 2023

(30) Foreign Application Priority Data

Dec. 3, 2019 (EP) .................................... 19213176

(51) Int. Cl.
*C10L 1/00* (2006.01)
*C10L 1/185* (2006.01)
(Continued)

(52) U.S. Cl.
CPC ............. *C10L 1/003* (2013.01); *C10L 1/1852* (2013.01); *C10M 171/007* (2013.01);
(Continued)

(58) Field of Classification Search
CPC ................... C10L 1/003; C10L 1/1852; C10L 2200/0423; C10L 2200/043;
(Continued)

(56) References Cited

U.S. PATENT DOCUMENTS 4,141,692 A   2/1979   Keller
5,827,805 A * 10/1998   Adams ................ C10M 159/12
44/410

(Continued)

FOREIGN PATENT DOCUMENTS

EP       0120641       10/1984
EP       0201368       11/1986
(Continued)

OTHER PUBLICATIONS

Riebe et al., "Atmospheric pressure chemical ionization of explosives induced by soft X-radiation in ion mobility spectrometry: mass spectrometric investigation of the ionization reactions of drift gasses, dopants and alkyl nitrates", J. Mass Spectrom. (2016), 51, 566-577.

(Continued)

*Primary Examiner* — Cephia D Toomer
(74) *Attorney, Agent, or Firm* — Muncy, Geissler, Olds & Lowe, P.C.

(57) ABSTRACT

The present invention relates to a method of marking a petroleum hydrocarbon by adding to and uniformly mixing (Continued)

with said petroleum hydrocarbon a chemical marker of general formula (I)

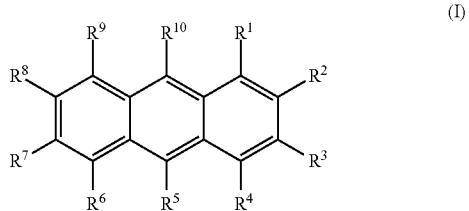

wherein two of the residues $R^1$-$R^{10}$ are independently of each other selected from $C_1$-$C_4$-alkoxy, and eight of the residues $R^1$-$R^{10}$ are independently of each other selected from the group consisting of hydrogen and $C_1$-$C_4$-alkyl, as well as to a composition of a petroleum hydrocarbon comprising a petroleum hydrocarbon and at least one chemical marker of general formula (I). The presence and concentration of the chemical marker of general formula (I) in the composition of the petroleum hydrocarbon can be advantageously determined by laser ionization coupled with mass spectrometry or by laser ionization coupled with ion mobility spectrometry.

10 Claims, 4 Drawing Sheets (51) Int. Cl.
*C10M 171/00* (2006.01)
*C10N 30/20* (2006.01)
(52) U.S. Cl.
CPC . *C10L 2200/0423* (2013.01); *C10L 2200/043* (2013.01); *C10L 2200/0438* (2013.01); *C10M 2207/04* (2013.01); *C10N 2030/20* (2013.01)

(58) Field of Classification Search
CPC .... C10L 2200/0438; C10L 2200/0446; C10M 171/007; C10M 2207/04; C10M 129/16; C10N 2030/20; C10N 2040/08; G01N 33/2882
See application file for complete search history.

(56) References Cited

U.S. PATENT DOCUMENTS

| 9,366,661 | B1 | 6/2016 | Conroy et al. |
| 2011/0290997 | A1* | 12/2011 | Green ...................... C10L 1/04 44/388 |
| 2012/0090225 | A1 | 4/2012 | Green et al. |
| 2014/0008164 | A1 | 1/2014 | Lai |
| 2014/0179955 | A1 | 6/2014 | Green et al. |
| 2017/0269056 | A1* | 9/2017 | Ciampini ........... G01N 25/4873 |

FOREIGN PATENT DOCUMENTS

| WO | 02098199 | 12/2002 |
| WO | 2004068113 | 8/2004 |
| WO | 2012153132 | 11/2012 |
| WO | 2012154646 | 11/2012 |
| WO | 2013003573 | 1/2013 |
| WO | 2014008164 | 1/2014 |
| WO | 2014081556 | 5/2014 |

OTHER PUBLICATIONS

Brendler et al., "Investigation of neuroleptics and other aromatic compounds by laser-based ion mobility mass spectrometry", Anal. Bional. Chem. 405, 7019, 2013, 11 pages.
International Search Report and Written Opinion issued with respect to application No. PCT/EP2020/083471, 2021.

* cited by examiner

METHOD OF MARKING A PETROLEUM HYDROCARBON

FIELD OF THE INVENTION

The present invention relates to the technical field of methods of marking a petroleum hydrocarbon with a chemical marker and chemically marked petroleum hydrocarbons.

BACKGROUND OF THE INVENTION

Marking of petroleum hydrocarbons with the scope of auditing the custody transfer of such products, to prevent and/or prove theft and/or counterfeiting is of great importance for the petroleum industry. In addition, this solution may be also used to control whether a distributor has sold an inexpensive petroleum hydrocarbon as an expensive petroleum hydrocarbon or has used an inexpensive petroleum hydrocarbon to dilute an expensive petroleum hydrocarbon.

Additionally, national governments are interested in technical solutions that allow to determine whether applicable taxes have been paid on petroleum hydrocarbons, whether tax exempt petroleum hydrocarbons are being sold as tax paid petroleum hydrocarbons or if they are being used to dilute tax paid petroleum hydrocarbons, and whether a petroleum hydrocarbon, which meets environmentally mandated specifications has been diluted with a product that does not meet such specifications.

A limited number of chemical markers for tagging petroleum hydrocarbons and m methods for detecting said markers in the tagged products have been described.

The use of halogenated compounds, such as halogenated alkanes, halogenated olefins and halogenated aromatic compounds (WO02098199A2), perfluorinated $C_9$-$C_{18}$ polycyclic hydrocarbons (EP0120641A2), chlorinated hydrocarbons and chlorocarbons (U.S. Pat. No. 4,141,692), and brominated or fluorinated benzene and naphthalene derivatives (WO2012153132A1), as tracers for marking a hydrocarbon liquid, as well as their detection by gas chromatography—mass spectrometry (WO2012153132A1), gas chromatography—electron capture detection (EP0120641A2, U.S. Pat. No. 4,141,692) or X-ray fluorescence (WO02098199A2) have been previously described.

Aryl ethers, including bis(alkyloxy)-1,1'-biphenyl derivatives (WO2013003573A1), bis(phenoxymethyl)-1,1'-biphenyl derivatives (US20120090225A1), alkyl aryl ethers and alkenyl aryl ethers (WO2014081556A1), ortho-phenyl phenol ethers (WO2012154646A1), tritylated alkyl aryl ethers (WO2014008164A1), bisphenol A substituted benzyl ethers (US20140179955A1), deuterated bis(4-(alkyloxy)phenyl) sulfane derivatives (U.S. Pat. No. 9,366,661B1) and deuterated 4,4'-oxybis((alkyloxy)benzene derivatives (U.S. Pat. No. 9,366,661B1) are also known as chemical markers for petroleum hydrocarbons. The detection of such type of chemical markers include gas-chromatography—flame ionization detection (WO2013003573A1), gas chromatography—mass spectrometry (US20120090225A1, WO2012154646A1, WO2014008164A1, US20140179955A1, U.S. Pat. No. 9,366,661B1) and two-dimensional gas chromatography coupled with mass spectrometry (WO2014081556A1).

Further, US patent application publication number US2014008164A1 describes the use of 4,4'-bis(benzyl)-1,1'-biphenyl derivatives as chemical markers for liquid hydrocarbons and gas chromatography as detection technique of such chemical markers.

US patent application publication number US2011290997A1 discloses the use of 1,3-diphenyl-2-buten-1-one derivatives for marking a petroleum hydrocarbon and gas chromatography-mass spectrometry for detection of such chemical markers.

International patent application publication number WO2004068113A2 describes a method of marking a fuel with a chemical marker of general formula RCAR', wherein R is a compound selected from the group consisting of alkyl, olefin, aryl, heterocycle and hydrogen; R' is a compound selected from the group consisting of alkyl, olefin, aryl, heterocycle and hydrogen; and wherein A is a compound selected from the group consisting of ketones, alcohol, amines, cyano, sulfate, nitrile, nitrate, halogen, organic acid, mercaptan, aldehyde, formyl, thiocyano, and isothiocyano, and the use of ion mobility spectrometry for detection of said chemical marker. The ion mobility spectrometry detection method described by WO2004068113A2 uses nickel 63 ($^{63}$Ni) as ionization source, which results in unselective ionization of the sample leading to difficult identification of the marker ion peak among the fuel matrix ion peaks.

The main disadvantage associated with the use of chemical markers whose detection and eventual quantification relies upon the use of the gas chromatography (GC) is that the GC column used in the separation of the marked petroleum hydrocarbon components has to be frequently replaced as a result of the high amount of petroleum hydrocarbon components compared to the chemical marker to be analyzed via said method. For the chemical markers whose detection and quantification techniques rely upon the use of gas chromatography—mass spectrometry (GC-MS), the frequent cleaning and/or replacement of the ionization source of the mass spectrometer is additionally required.

European patent application publication number EP0201368A1 describes the use of anthraquinone derivatives for marking diesel oil and similar oil products. Detection of the presence of an anthraquinone derivative in the diesel oil relies upon the visual observation of a red color which can be obtained by treating the marked diesel oil with an alkaline solution of sodium dithionite, followed by stirring and ten minutes decantation. The quantification of the anthraquinone derivative in the marked diesel oil further requires an extraction step, followed by a measurement of the color intensity by spectrophotometry. The detection and quantification methods disclosed by EP0201368A1 are time-consuming and do not enable the identification of the anthraquinone derivative used for marking the diesel oil.

Because of the limited number of currently available chemical markers for tagging petroleum hydrocarbon products and the different disadvantages associated with some of them, such as light and heat instability in the marked petroleum hydrocarbon, insolubility in the marked petroleum hydrocarbon, toxicity, unsatisfactory counterfeit-resilience, unsatisfactory laundering resistance, lengthy detection and quantification methods, there is a constant need for the development of additional chemical markers to satisfy the high demand from government bodies and the petroleum industry.

In selecting a suitable chemical marker, several factors must be taken into consideration. Among the major ones are: cost, ease of detection, identification and quantification, stability, solubility and compatibility with the petroleum hydrocarbon, inertness to air, water and normal soil components, corrosivity, volatility and toxicity. Additionally, the chemical markers for low tax petroleum hydrocarbons, should not be laundered by an economically viable process.

The problem addressed by the present invention is to provide additional chemical compounds for marking petroleum hydrocarbons to prevent counterfeiting of said petroleum hydrocarbons.

SUMMARY OF THE INVENTION

Accordingly, it is the object of the present invention to provide a composition of a petroleum hydrocarbon comprising:
  a petroleum hydrocarbon; and
  at least one chemical marker of general formula (I) uniformly mixed with the petroleum hydrocarbon

(I)

wherein two of the residues $R^1$-$R^{10}$ are independently of each other selected from $C_1$-$C_4$-alkoxy, and eight of the residues $R^1$-$R^{10}$ are independently of each other selected from the group consisting of hydrogen and $C_1$-$C_4$-alkyl.

Minute quantities of the chemical markers of general formula (I) in a petroleum hydrocarbon are easily detectable, identifiable, and quantifiable by laser ionization at a wavelength of between about 300 nm and about 370 nm coupled with mass spectrometry, or by laser ionization at a wavelength of between about 300 nm and about 370 nm coupled with ion mobility spectrometry. Sample vaporization followed by laser ionization at a wavelength of between about 300 nm and about 370 nm coupled with mass spectrometry, or by laser ionization at a wavelength of between about 300 nm and about 370 nm coupled with ion mobility spectrometry, enables identification and quantification of the dialkoxy-anthracene of general formula (I) in a petroleum hydrocarbon, and thereby confirming the authenticity of said petroleum hydrocarbon and/or detecting the adulteration of said petroleum hydrocarbon. Detection of the peak corresponding to the ion ($M^+$) of the dialkoxy-anthracene of general formula (I) in the mass spectrum or the ion mobility spectrum (i.e. identification of the dialkoxy-anthracene of general formula (I)) is indicative of the authenticity of said petroleum hydrocarbon. For certain applications, such as chemical marking of low tax petroleum hydrocarbon, detection of the presence of the dialkoxy-anthracene of general formula (I) in the petroleum hydrocarbon is typically considered a sufficient condition for acknowledging the authenticity of said petroleum hydrocarbon. In an equivalent manner, detection of the presence of a dialkoxy-anthracene of general formula (I) used for chemically marking low tax petroleum hydrocarbon in an alleged high tax petroleum hydrocarbon (i.e. a petroleum hydrocarbon that is not supposed to contain said chemical marker) is a sufficient condition for acknowledging that the high tax petroleum hydrocarbon is not authentic. As well known to the skilled person adulteration of a petroleum hydrocarbon refers to altering, mixing, diluting, laundering, etc., of the petroleum hydrocarbon. In some cases, a petroleum hydrocarbon (e.g. a petroleum hydrocarbon taxed at a higher rate) can be combined (e.g. illegally) with another petroleum hydrocarbon (e.g. an untaxed petroleum hydrocarbon or petroleum hydrocarbon taxed at a lower rate) or solvent to form an adulterated (e.g., altered, mixed, diluted, laundered, etc.) petroleum hydrocarbon. For example, a petroleum hydrocarbon can be mixed with one or more other petroleum hydrocarbons, solvents, and the like, or combinations thereof. If undetected, the adulterated petroleum hydrocarbon can be sold, sometimes illegally, at the price of the petroleum hydrocarbon taxed at the higher rate to yield a profit. In some instances, the adulterated petroleum hydrocarbon can be potentially hazardous for the user, such as for example when a hazardous solvent is used for adulterating the petroleum hydrocarbon. In other instances, the petroleum hydrocarbon can be treated or laundered in an attempt to remove identifying features, such as chemical markers from the petroleum hydrocarbon (e.g. to disguise the origin of the petroleum hydrocarbon the amount of tax paid on the petroleum hydrocarbon, etc.) before the petroleum hydrocarbon is mixed with another petroleum hydrocarbon to form an adulterated petroleum hydrocarbon. Chemical marking of a petroleum hydrocarbon with a compound of general formula (I) renders the above-described adulteration activities difficult and constitutes an extremely useful tool for proving and/or preventing counterfeiting of said petroleum hydrocarbon.

The dialkoxy-anthracene of general formula (I) are inert to air, water and soil components, as well as conventional petroleum hydrocarbon components, and they are non-corrosive. Furthermore, they are commercially available at a low cost or can be synthesized by well-established organic chemistry methods, and their detection and quantification methods do not suffer from the drawbacks encountered for the GC-MS based detection and quantification methods. Moreover, the chemical markers of general formula (I) are relatively non-toxic, do not produce harmful products upon combustion and exhibit excellent laundering resistance to chemical reagents, such as acids and alkalis.

A further aspect of the present invention is directed to a method for marking a petroleum hydrocarbon to prevent counterfeiting of said petroleum hydrocarbon, wherein said method comprises adding to and uniformly mixing with said petroleum hydrocarbon at least one chemical marker of general formula (I)

(I)

wherein two of the residues $R^1$-$R^{10}$ are independently of each other selected from $C_1$-$C_4$-alkoxy, and eight of the residues $R^1$-$R^{10}$ are independently of each other selected from the group consisting of hydrogen and $C_1$-$C_4$-alkyl.

DETAILED DESCRIPTION

Definitions

The following definitions are to be used to interpret the meaning of the terms discussed in the description and recited in the claims.

As used herein, the article "a/an" indicates one as well as more than one and does not necessarily limit its referent noun to the singular.

As used herein, the term "about" means that the amount or value in question may be the specific value designated or some other value in its neighbourhood. Generally, the term "about" denoting a certain value is intended to denote a range within ±5% of the value. As one example, the phrase "about 100" denotes a range of 100±5, i.e. the range from 95 to 105. Preferably, the range denoted by the term "about" denotes a range within ±3% of the value, more preferably ±1%. Generally, when the term "about" is used, it can be expected that similar results or effects according to the invention can be obtained within a range of ±5% of the indicated value.

As used herein, the term "and/or" means that either all or only one of the elements of said group may be present. For example, "A and/or B" means "only A, or only B, or both A and B". In the case of "only A", the term also covers the possibility that B is absent, i.e. "only A, but not B".

The term "comprising" as used herein is intended to be non-exclusive and open-ended. Thus, for instance a solution comprising a compound A may include other compounds besides A. However, the term "comprising" also covers, as a particular embodiment thereof, the more restrictive meanings of "consisting essentially of" and "consisting of", so that for instance "a solution comprising A, B and optionally C" may also (essentially) consist of A and B, or (essentially) consist of A, B and C.

Where the present description refers to "preferred" embodiments/features, combinations of these "preferred" embodiments/features are also deemed to be disclosed as long as the specific combination of "preferred" embodiments/features is technically meaningful.

Surprisingly, it has been found that minute quantities of a dialkoxyanthracene derivative of general formula (I) in a petroleum hydrocarbon can be detected, identified and quantified by laser ionization at a wavelength of between about 300 nm and about 370 nm coupled with mass spectrometry, or by laser ionization at a wavelength of between about 300 nm and about 370 nm coupled with ion mobility spectrometry. Additionally, it has been found that the dialkoxyanthracene derivatives of general formula (I) are soluble in a variety of petroleum hydrocarbons at marking concentrations of commercial interest, exhibit excellent laundering resistance to chemical reagents, such as acids and alkalis, and consequently, they are useful for chemically marking petroleum hydrocarbons.

The present invention provides a composition of a petroleum hydrocarbon comprising:
    a petroleum hydrocarbon; and
    at least one chemical marker of general formula (I) uniformly mixed with the petroleum hydrocarbon (I)

wherein two of the residues $R^1$-$R^{10}$ are independently of each other selected from $C_1$-$C_4$-alkoxy, and eight of the residues $R^1$-$R^{10}$ are independently of each other selected from the group consisting of hydrogen and $C_1$-$C_4$-alkyl.

Another aspect of the invention provides a method for marking a petroleum hydrocarbon to prevent counterfeiting of said petroleum hydrocarbon, wherein said method comprises adding to and uniformly mixing with said petroleum hydrocarbon at least one chemical marker of general formula (I)

(I)

wherein two of the residues $R^1$-$R^{10}$ are independently of each other selected from $C_1$-$C_4$-alkoxy, and eight of the residues $R^1$-$R^{10}$ are independently of each other selected from the group consisting of hydrogen and $C_1$-$C_4$-alkyl.

The term "petroleum hydrocarbon" refers to products having a predominantly hydrocarbon composition, although they may contain minor amounts of oxygen, nitrogen, sulfur or phosphorus. As used herein, the term "petroleum hydrocarbon" includes crude oils, as well as products derived from petroleum refining processes. Preferably, a "petroleum hydrocarbon" includes without limitation crude oil, lubricating oil, hydraulic fluid, brake fluid, gasoline, diesel fuel, kerosene, jet fuel, heating oil and heavy fuel oil. More preferably, the petroleum hydrocarbon is selected from the group consisting of gasoline, diesel fuel, kerosene, and jet fuel, and even more preferably from the group consisting of gasoline and diesel fuel.

The term "$C_1$-$C_4$-alkyl" as used herein refers to a saturated linear or branched-chain monovalent hydrocarbon radical of one to four carbon atoms ($C_1$-$C_4$). Examples of $C_1$-$C_4$-alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, iso-propyl, —$CH(CH_3)_2$), 1-butyl (n-Bu, n-butyl. —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$) and 2-methyl-2-propyl (t-Bu, t-butyl, —$C(CH_3)_3$). The term "$C_1$-$C_4$-alkyloxy" means a $C_1$-$C_4$-alkyl group, wherein the $C_1$-$C_4$-alkyl is as defined herein, that is linked to the rest of a molecule or to another group through an oxygen atom. Illustrative examples of $C_1$-$C_4$-alkyloxy include methoxy, ethoxy, n-propoxy, iso-propoxy, n-butoxy, iso-butoxy, sec-butoxy and tert-butoxy.

Preferably, the at least one chemical marker of general formula (I) is characterized by a boiling point lower than about 600° C. at 760 mm Hg, more preferably lower than 500° C. at 760 mm Hg, and even more preferably lower than 450° C. at 760 mm Hg. Such a chemical marker is particularly useful for marking subsidized petroleum hydrocarbons, such as subsidized kerosene and subsidized diesel, because it renders economically not viable the removal of the chemical marker from the subsidized petroleum via distillation that is known as one the most used techniques for eliminating the chemical markers from the subsidized petroleum hydrocarbons.

Figure 1A:
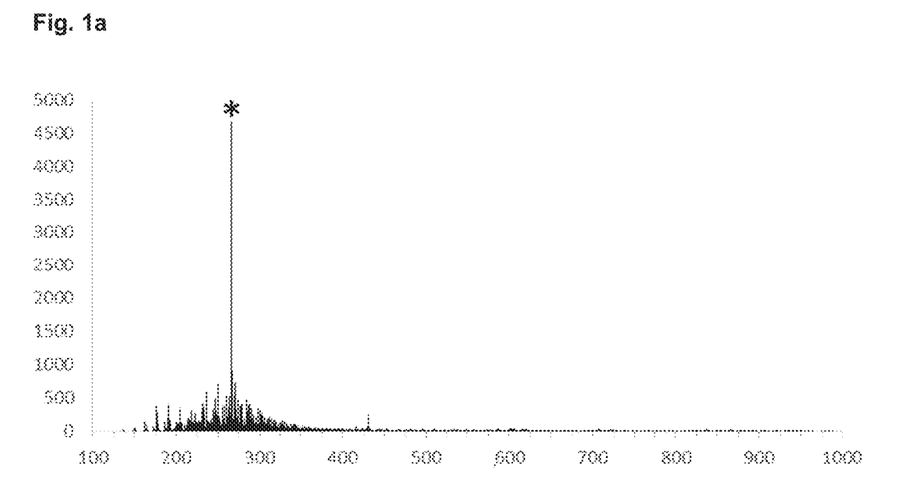
FIG. 1a illustrates the mass spectrum of a composition of diesel containing the chemical marker 2-ethyl-9,10-dimethoxy-anthracene obtained by laser ionization at 308 nm coupled with mass spectrometry. The peak corresponding to the ion (M⁺) of the chemical marker 2-ethyl-9,10-dimethoxy-anthracene (m/z of 266) is indicated by a "*".
Figure 1B:
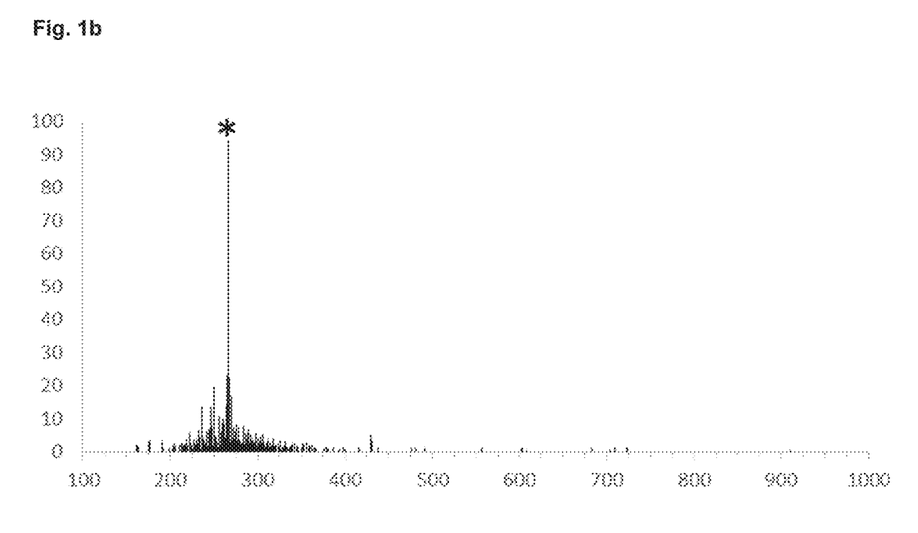
FIG. 1b illustrates the mass spectrum of a composition of diesel containing the chemical marker 2-ethyl-9,10-dimethoxy-anthracene obtained by laser ionization at 337 nm coupled with mass spectrometry. The peak corresponding to the ion (M⁺) of the chemical marker 2-ethyl-9,10-dimethoxy-anthracene (m/z of 266) is indicated by a "*".
Figure 1C:
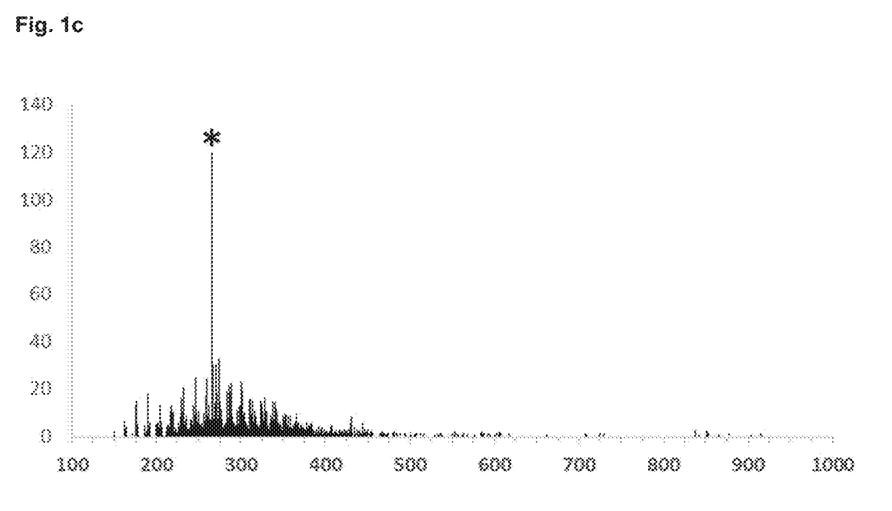
FIG. 1c illustrates the mass spectrum of a composition of diesel containing the chemical marker 2-ethyl-9,10-dimethoxy-anthracene obtained by laser ionization at 355 nm coupled with mass spectrometry. The peak corresponding to the ion (M⁺) of the chemical marker 2-ethyl-9,10-dimethoxy-anthracene (m/z of 266) is indicated by a "*".
Figure 1D:
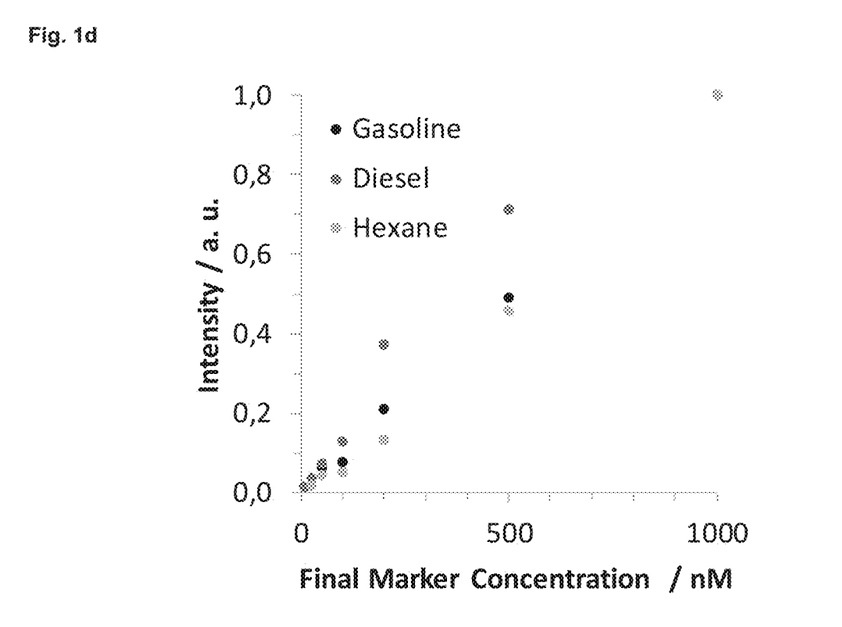
FIG. 1d illustrates the variation of the intensity of the peak corresponding to the molecular ion (M⁺) of the chemical marker 2-ethyl-9,10-dimethoxy-anthracene with the concentration of the chemical marker in a composition of gasoline, a composition of diesel and a composition of hexane, respectively. The compositions of diesel containing the chemical marker 2-ethyl-9,10-dimethoxy-anthracene at different concentrations were analyzed by laser ionization at 355 nm coupled with mass spectrometry.

As attested for example by FIG. 1a-FIG. 1d, the dialkoxyanthracene derivatives of general formula (I) are easily detectable, identifiable and quantifiable in minute quantities by laser ionization at a wavelength of between about 300 nm and about 370 nm coupled with mass spectrometry. Moreover, as illustrated for example by FIG. 2a-FIG. 2c, the dialkoxyanthracene derivatives of general formula (I) are easily detectable, identifiable and quantifiable in minute quantities also by laser ionization at a wavelength of between about 300 nm and about 370 nm coupled with ion mobility spectrometry. As shown by FIG. 1a-FIG. 1c, FIG. 2a and FIG. 2b, the dialkoxyanthracene derivatives of general formula (I) can be selectively ionized in a composition of petroleum hydrocarbon, following sample vaporization, by illumination with pulsed laser light having a wavelength of 308 nm, 337 nm and 355 nm, respectively. Selective ionization of the dialkoxyanthracene derivatives of general formula (I) in a composition of petroleum hydrocarbon can be achieved by illumination of a volatile sample of said composition with pulsed laser light having any wavelength of between about 300 nm and about 370 nm, such as for example 308 nm, 337 nm and 355 nm. As illustrated by FIG. 2c, the detection, identification and quantification of a chemical marker of general formula (I) is independent of the petroleum hydrocarbon to which said chemical marker is added. Thus, the dialkoxyanthracene derivative of general formula (I) can serve as a chemical marker for a variety of petroleum hydrocarbons.

In addition, the dialkoxyanthracene derivatives of general formula (I) are inert to air, water and soil components, as well as conventional petroleum hydrocarbon components, and they are non-corrosive. Further, they are commercially available at relatively low cost or can be obtained by well-established organic chemistry methods, and their detection and quantification methods do not suffer from the drawbacks encountered for the GC-MS based detection and quantification methods. Moreover, the dialkoxyanthracene derivatives of general formula (I) are relatively non-toxic, do not produce harmful products upon combustion, are soluble in a variety of petroleum hydrocarbons at marking concentrations of commercial interest, exhibit excellent laundering resistance to chemical reagents, such as acids and alkalis and consequently, they are useful chemical markers for petroleum hydrocarbons.

Preferably, the concentration of the at least one chemical marker of general formula (I) in the composition claimed and described herein and the method of marking claimed and described herein is of at least 1 µM (micromolar), Depending on the petroleum hydrocarbon to be marked and the method used for the detection, identification and quantification of the chemical marker, namely laser ionization at a wavelength of between about 300 nm and about 370 nm coupled with mass spectrometry or laser ionization at a wavelength of between about 300 nm and about 370 nm coupled with ion mobility spectrometry, higher concentration of the at least one chemical marker of general formula (I) in the composition of petroleum hydrocarbon may be required. Owing to the high solubility of the chemical marker of general formula (I) in a variety of petroleum hydrocarbons, even high marking concentration of about 1 mM (millimolar) may be considered. It remains within the skills of the person skilled in the art of petroleum hydrocarbon marking to determine via routine work an adequate marking concentration for a specific chemical marker of general formula (I), taking into account the type of petroleum hydrocarbon to be marked, the method used for the detection and quantification of said specific chemical marker, namely laser ionization at a wavelength of between about 300 nm and about 370 nm coupled with mass spectrometry or laser ionization at a wavelength of between about 300 nm and about 370 nm coupled with ion mobility spectrometry, as well as the cost of the chemical marker.

In the general formula (I), the two $C_1$-$C_4$-alkoxy substituents may be positioned at any position on the anthracene core. In other words, dialkoxyanthracene derivative of general formula (I), wherein the residues $R^1$ and $R^2$ are independently of each other selected from $C_1$-$C_4$-alkoxy, or wherein the residues $R^1$ and $R^3$ are independently of each other selected from $C_1$-$C_4$-alkoxy, or wherein the residues $R^1$ and $R^4$ are independently of each other selected from $C_1$-$C_4$-alkoxy, or wherein the residues $R^1$ and $R^5$ are independently of each other selected from $C_1$-$C_4$-alkoxy, or wherein the residues $R^1$ and $R^6$ are independently of each other selected from $C_1$-$C_4$-alkoxy, or wherein the residues $R^1$ and $R^7$ are independently of each other selected from $C_1$-$C_4$-alkoxy, or wherein the residues $R^1$ and $R^9$ are independently of each other selected from $C_1$-$C_4$-alkoxy, or wherein the residues $R^1$ and $R^9$ are independently of each other selected from $C_1$-$C_4$-alkoxy, or wherein the residues $R^1$ and $R^{10}$ are independently of each other selected from $C_1$-$C_4$-alkoxy, or wherein the residues $R^2$ and $R^3$ are independently of each other selected from $C_1$-$C_4$-alkoxy, or wherein the residues $R^2$ and $R^5$ are independently of each other selected from $C_1$-$C_4$-alkoxy, or wherein the residues $R^2$ and $R^7$ are independently of each other selected from $C_1$-$C_4$-alkoxy, or wherein the residues $R^2$ and $R^8$ are independently of each other selected from $C_1$-$C_4$-alkoxy, or wherein the residues $R^2$ and $R^{19}$ are independently of each other selected from $C_1$-$C_4$-alkoxy, or wherein the residues $R^5$ and $R^{10}$ are independently of each other selected from $C_1$-$C_4$-alkoxy are useful chemical markers for petroleum hydrocarbons.

A preferred embodiment according to the present invention is directed to a composition and a method of marking a petroleum hydrocarbon as claimed and described herein, wherein the residues $R^5$ and $R^{10}$ are independently of each other selected from $C_1$-$C_4$-alkoxy. Hence, a preferred embodiment according to the present invention is directed to a composition and method of marking a petroleum hydrocarbon as claimed and described herein, wherein the at least one chemical marker is of general formula (II)

(II)

wherein the residues $R^1$-$R^4$ and $R^6$-$R^9$ are independently of each other selected from the group consisting of hydrogen and $C_1$-$C_4$-alkyl and the residues $R^{11}$ and $R^{12}$ are independently of each other selected from $C_1$-$C_4$-alkyl.

In the general formula (II), the residues $R^6$-$R^9$ may represent hydrogen, or the residues $R^1$-$R^4$ and $R^6$-$R^9$ may independently of each other represent $C_1$-$C_4$-alkyl, or the residues $R^1$-$R^4$ and $R^6$-$R^9$ may represent hydrogen.

A further preferred embodiment according to the present invention is directed to a composition and a method for marking a petroleum hydrocarbon as claimed and described herein, wherein the at least one chemical marker is of general formula (III)

(III)

wherein the residue $R^2$ is selected from the group consisting of hydrogen and $C_1$-$C_4$-alkyl, and the residues $R^{11}$ and $R^{12}$ are independently of each other selected from $C_1$-$C_4$-alkyl.

Preferably, in general formula (II), as well as in the general formula (III), the residues $R^{11}$ and $R^{12}$ are the same.

Examples of the at least one chemical marker of general formula (I) that can be used in the composition and the method for marking a petroleum hydrocarbon claimed and described herein, include, but are not limited to: 2-methyl-9,10-dimethoxyanthracene (CAS no.: 26708-05-4; provider: Chemieliva Pharmaceutical Co.); 2-ethyl-9,10-dimethoxy-anthracene (CAS no.: 26708-04-3; provider: Aldrich); 2-(1,1-dimethyl-ethyl)-9,10-dimethoxyanthracene (CAS no.: 62770-63-2; provider: Chemieliva Pharmaceutical Co.); 2-ethyl-9,10-diethoxyanthracene (CAS no.: 205515-07-7; provider: Chemieliva Pharmaceutical Co.); 9,10-dimethoxy-anthracene (CAS no.: 2395-97-3; provider: Chemieliva Pharmaceutical Co.); 9,10-diethoxyanthracene (CAS no.: 68818-86-0; provider: ASW MedChem); 9,10-bis(1-methylethoxy)-anthracene (CAS no.: 134767-44-5; provider: Chemieliva Pharmaceutical Co.); 9,10-bis(1,1-dimethylethoxy)-anthracene (CAS no.: 873914-42-2; provider: Shanghai Chemhere Co.); 9,10-dibutoxy-anthracene (CAS no.: 76275-14-4; provider: Chemieliva Pharmaceutical Co.); 9-ethoxy-10-methoxy-anthracene (CAS no.: 106500-38-3; provider: Chemieliva Pharmaceutical Co.), 9,10-dimethoxy-1,4,5,8-tetramethyl-anthracene (CAS no.: 76466-58-5; provider: Chemieliva Pharmaceutical Co.); 9,10-dimethoxy-1,2,3,4,5,6,7,8-octamethyl-anthracene (CAS no.: 75670-41-6; provider: Chemieliva Pharmaceutical Co.); 9,10-dimethoxy-1,2,3,4-tetramethyl-anthracene (CAS no.: 72049-50-4; provider: Chemieliva Pharmaceutical Co.); 2,6-dimethyl-9,10-dimethoxyanthracene (CAS no.: 1221786-94-2; provider: Rare Chemicals GmbH); 1,2-dimethoxy-anthracene (CAS no.: 132814-35-8; provider: Shanghai Chemhere Co.); 1,3-dimethoxyanthracene (CAS no.: 144493-74-3; provider: Chemieliva Pharmaceutical Co.); 1,4-dimethoxy-9-ethyl-anthracene (CAS no.: 107328-77-8, provider: Chemieliva Pharmaceutical Co.); 1,4-diethoxy-anthracene (CAS no.: 75830-00-1; provider: Chemieliva Pharmaceutical Co.); 1,5-dimethoxy-anthracene (CAS no.: 16294-32-9; provider: Chemieliva Pharmaceutical Co.); 1,5-diethoxy-anthracene (CAS no.: 75829-95-7; provider: Chemieliva Pharmaceutical Co.); 1,8-dimethoxy-anthracene (CAS no.: 16294-34-1; provider: Chemieliva Pharmaceutical Co); 1,8-diethoxy-anthracene (CAS no.: 75829-96-8; provider: Chemieliva Pharmaceutical Co.); 1,8-dimethoxy-3-methyl-anthracene (CAS no.: 144493-77-6; provider: Chemieliva Pharmaceutical Co.), 1,8-dimethoxy-2,7-dimethyl-anthracene (CAS no.: 1202400-23-4; provider: Chemieliva Pharmaceutical Co.); 2,3-dimethoxy-anthracene (CAS no.: 51790-19-3; provider: Chemieliva Pharmaceutical Co.); 2,3-diethoxy-anthracene (CAS no.: 863889-35-4; provider: Chemieliva Pharmaceutical Co.); 2,6-dimethoxy-anthracene (CAS no.: 36319-03-6; provider: Chemieliva Pharmaceutical Co.); 2,6-diethoxy-anthracene (CAS no.: 75830-05-6; provider: Chemieliva Pharmaceutical Co.); 2,6-dimethoxy-9-methyl-anthracene (CAS no.: 110038-59-0; provider: Chemieliva Pharmaceutical Co.); 2,6-dimethoxy-9,10-dimethyl-anthracene (CAS no.: 105858-59-1; provider: Chemieliva Pharmaceutical Co.); 2,6-dipropoxy-anthracene (CAS no.: 1395499-89-4; provider: Chemieliva Pharmaceutical Co.); 2,6-dibutoxy-anthracene (CAS no.: 134277-70-6; provider: Chemieliva Pharmaceutical Co.); and 2,7-dimethoxy-anthracene (CAS no.: 55360-36-6; provider: Chemieliva Pharmaceutical Co.).

The composition claimed and described herein may contain a further chemical marker, which is structurally different from the herein described dialkoxy-anthracene derivative of general formula (I). Use of multiple chemical markers facilitates incorporation into the petroleum hydrocarbon of coded information that may be used to identify the origin and other characteristics of the petroleum hydrocarbon. The code comprises the identities and relative amounts, e.g. fixed integer ratios, of the chemical markers. One, two, three or more chemical marker compounds that may be also detectable, identifiable and quantifiable by laser ionization at a wavelength of between about 300 nm and about 370 nm (for e.g. 308 nm, 337 nm, 355 nm) coupled with mass spectrometry or by laser ionization at a wavelength of between about 300 nm and about 370 nm (for e.g. 308 nm, 337 nm, 355 nm) coupled with ion mobility spectrometry may be used to form the code. The at least one dialkoxy-anthracene derivative of general formula (I) may be combined with chemical markers, such as:

i) a diphenyl-polyene derivative of general formula (IV)

(IV)

wherein the residues $R^{13}$-$R^{22}$ are independently of each other selected from the group consisting of hydrogen and $C_1$-$C_4$ alkyl; the residue -L- represents —$CR^a$═$CR^b$—, wherein $R^a$ and $R^b$ are independently of each other selected from the group consisting of hydrogen and methyl; and n is an integer comprised between 2 and 6;

ii) an aromatic compound substituted by one or more N,N-disubstituted amino groups, wherein the substituents of the one or more N,N-disubstituted amino groups are independently of each other selected from $C_1$-$C_6$-alkyl; or iii) a naphthacene derivative of general formula (V)

(V)

wherein the residues $R^{23}$-$R^{34}$ are independently of each other selected from the group consisting of hydrogen, $C_1$-$C_4$-alkyl and phenyl optionally substituted by one or more groups selected from $C_1$-$C_4$-alkyl, with the proviso that at least two of the residues $R^{23}$-$R^{34}$ represent a phenyl optionally substituted by one or more groups selected from $C_1$-$C_4$-alkyl.

Preferably, the diphenyl-polyene of general formula (IV) is characterized by a boiling point lower than about 600° C. at 760 mm Hg, more preferably lower than about 500° C. at 760 mm Hg, and even more preferably lower than 450° C. at 760 mm Hg. Examples of diphenyl-polyene of general formula (IV) include but are not limited to: 6-diphenyl-1,3,5-hexatriene (CAS, no.: 1720-32-7; provider: Sigma Aldrich); (1E,3E)-1,4-diphenylbuta-1,3-diene (CAS no.: 538-81-8; provider: ASW MedChem); ((1E,3E)-penta-1,3-diene-1,4-diyl)dibenzene (CAS no.: 23637-42-5; provider: Chemileva Pharmaceutical); 1-methyl-4-((1E,3E)-4-phenylbuta-1,3-dien-1-yl)benzene (CAS no.: 37985-11-8; provider: Chemileva Pharmaceutical); ((1E,3E)-2-methylbuta-1,3-diene-1,4-diyl)dibenzene (CAS no.: 23637-43-6; provider: Chemileva Pharmaceutical); ((2E,4E)-hexa-2,4-diene-2,5-diyl)dibenzene (CAS no.: 16914-12-8; provider: Chemileva Pharmaceutical); 1-methyl-2-(1E,3E)-4-phenylbuta-1,3-dien-1-yl)benzene (CAS no.: 93333-38-1; provider: Chemileva Pharmaceutical); 1-methyl-3-((1E,3E)-4-phenylbuta-1,3-dien-1-yl)benzene (CAS no.: 82102-26-9; provider: Chemileva Pharmaceutical); (1E,3E)-1,4-di-o-tolylbuta-1,3-diene (CAS no.: 848354-92-7; provider: Shanghai Chemhere Co.); (1E,3E)-1,4-di-m-tolylbuta-1,3-diene (CAS no.: 1261146-08-0; provider: Chemileva Pharmaceutical); (1E,3E)-1,4-di-p-tolylbuta-1,3-diene (CAS no.: 72033-82-0; provider: Chemileva Pharmaceutical); ((1E,3E)-2-methylpenta-1,3-diene-1,4-diyl)dibenzene (CAS no.: 117847-11-7; provider: Chemileva Pharmaceutical); ((1E,3E)-2,3-dimethylbuta-1,3-diene-1,4-diyl)dibenzene (CAS no.: 54631-95-7; provider: Shanghai Chemhere Co.); 1-methyl-4-((1E,3E)-3-methyl-4-phenylbuta-1,3-diem-1-yl)benzene (CAS no.: 916764-21-1; provider: Chemileva Pharmaceutical); (1E,3E)-1,4-di-m-tolylbuta-1,3-diene (CAS no.: 12611146-10-4; provider; Chemileva Pharmaceutical); 4,4'-((1E,3E)-2-methylbuta-1,3-diene-1,4-diyl)bis(methylbenzene) (CAS no.: 102080-29-5; provider: Chemileva Pharmaceutical); (1E,3E)-1,4-dimesitylbuta-1,3-diene (CAS no.: 1261146-09-1; provider: Chemileva Pharmaceutical); 4,4'-((2E,4E)-hexa-2,4-diene-2,5-diyl)bis(methylbenzene) (CAS no.: 110746-28-6; provider: Chemileva Pharmaceutical); 1,2,4,5-tetramethyl-3-((1E,3E)-4-phenylbuta-1,3-dien-1-Abenzene (CAS no.: 39117-47-0; provider: Chemileva Pharmaceutical); (1E,3E)-1,4-bis(2,4,5-trimethylphenyl)buta-1,3-diene (CAS no.: 96214-75-4; provider: Chemileva Pharmaceutical); (1Z,3Z)-1,4-diphenylbuta-1,3-diene (CAS no.: 5807-76-1; provider: Chemileva Pharmaceutical); (1Z,3Z)-1,4-di-o-tolylbuta-1,3-diene (CAS no.: 1006055-80-6; provider: Chemileva Pharmaceutical); (1Z,3E)-1,4-diphenylbuta-1,3-diene (CAS no.: 5808-05-9; provider: Chemileva Pharmaceutical); ((1E,3Z)-penta-1,3-diene-1,4-diyl)dibenzene (CAS no.: 40391-41-1; provider: Chemileva Pharmaceutical); ((1Z,3E)-2-methylbuta-1,3-diene-1,4-diyl)dibenzene (CAS no.: 83897-70-5; provider: Chemileva Pharmaceutical); 1-methyl-4-((1Z,3E)-4-phenylbuta-1,3-dien-1-yl)benzene (CAS no.: 57668-27-6; provider: Chemileva Pharmaceutical); ((2Z,4E)-hexa-2,4-diene-2,5-diyl)dibenzene (CAS no.: 84174-09-4; provider: Chemileva Pharmaceutical); ((1E,3E)-2,3-dimethylbuta-1,3-diene-1,4-diyl)dibenzene (CAS no.: 38023-36-8; provider: Chemileva Pharmaceutical); (1E,3E,5E,7E)-1,8-diphenylocta-1,3,5,7-tetraene (CAS no.: 22828-29-1; provider: Chemileva Pharmaceutical); (1E,3E,5E)-1,6-diphenylhexa-1,3,5-triene (CAS no.: 17329-15-6; provider: ASW MedChem); ((1E,3E,5E)-3-methylhexa-1,3,5-triene-1,6-diyl)dibenzene (CAS no.: 155337-76-1; provider: Aurora Fine Chemicals LLC); ((1E,3E,5E)-hepta-1,3,5-triene-1,6-diyl)dibenzene (CAS no.: 140654-06-4; provider: Chemileva Pharmaceutical); 1-methyl-4-((1E,3E,5E)-6-phenylhexa-1,3,5-trien-1-yl)benzene (CAS no.: 36288-10-5; provider: Chemileva Pharmaceutical); 1-methyl-3-(6-phenylhexa-1,3,5-trien-1-yl)benzene (CAS no.: 95278-12-9; provider: Chemileva Pharmaceutical); 1-methyl-2-(6- phenylhexa-1,3,5-trien-1-yl)benzene (CAS no.: 95278-13-0; provider: Chemileva Pharmaceutical); 1,6-di-p-tolylhexa-1,3,5-triene (CAS no.: 31382-31-7; provider: Chemileva Pharmaceutical); 3,4-dimethylhexa-1,3,5-triene-1,6-diyl) dibenzene (CAS no.: 1295646-09-1; provider: Chemileva Pharmaceutical); 1,3-dimethyl-5-(6-phenylhexa-1,3,5-trien-1-yl)benzene (CAS no.: 63296-77-5; provider: Chemileva Pharmaceutical); 1-isopropyl-4-(6-(p-tolylhexa-1,3,5-trien-1-Abenzene (CAS no.: 558453-19-3; provider: Shanghai Chemhere Co.); 2,4-dimethyl-1-(6-phenylhexa-1,3,5-trien-1-yl)benzene (CAS no.: 63296-78-6; provider: Chemileva Pharmaceutical); (1Z,3E,5Z)-1,6-diphenylhexa-1,3,5-triene (CAS no.: 170080-16-7; provider: Chemileva Pharmaceutical); (1Z,3Z,5E)-1,6-diphenylhexa-1,3,5-triene (CAS no.: 205808-71-5; provider: Chemileva Pharmaceutical); (1Z,3Z,5Z)-1,6-diphenylhexa-1,3,5-triene (CAS no.: 170080-17-8; provider: Chemileva Pharmaceutical); ((1E,3E,5E)-2,3-dimethylhexa-1,3,5-triene-1,6-diyl)dibenzene (CAS no.: 57833-31-5; provider: Chemileva Pharmaceutical); (1E,3E,5E,7E)-1,8-di-p-tolylocta-1,3,5,7-tetraene (CAS no.: 82720-17-0; provider: Chemileva Pharmaceutical); 1-methyl-4-((1E,3E,5E,7E)-8-phenylocta-1,3,5,7-tetraen-1-Abenzene (CAS no.: 94871-35-9; provider: Chemileva Pharmaceutical); ((1E,3Z,5E,7E)-2,7-dimethylocta-1,3,5,7-tetraene-1,8-diyl)dibenzene (CAS no.: 82720-21-6; provider: Chemileva Pharmaceutical); (1E,3E,5E,7E,9E)-1,10-diphenyldeca-1,3,5,7,9-pentaene (CAS no.: 20576-64-1; provider: Chemileva Pharmaceutical); (3,8-dimethyldeca-1,3,5,7,9-pentaene-1,10-diyl)dibenzene (CAS no.: 1884-48-6; provider: Chemileva Pharmaceutical); and (1E,3E,5E,7E,9E,11E)-1,12-diphenyldodeca-1,3,5,7,9,11-hexaene (CAS no.: 20576-65-2; provider: Shanghai Chem here Co.).

Additionally, it is preferred that the aromatic compound substituted by one or more NA-disubstituted amino groups exhibits also a boiling point lower than about 600° C. at 760 mm Hg, preferably lower than 500° C. at 760 mm Hg, and more preferably lower than 450° C. at 760 mm Hg. Examples of the aromatic compound substituted by one or more N,N-disubstituted amino groups, include but are not limited to: N,N-dimethylbenzenamine (CAS no.: 121-69-7; provider: ASW MedChem); $N^1,N^1,N^4,N^4$-tetramethyl-1,4-benzenediamine (CAS no.: 100-22-1; provider: ASW MedChem); $N^1,N^1$-diethyl-$N^4,N^4$-dimethyl-1,4-benzenediamine (CAS no.: 5775-53-1; provider: Chemieliva Pharmaceutical); $N^1,N^1,N^4,N^4$-tetraethyl-1,4-benzenediamine (CAS no.: 18996-77-5; provider: Chemieliva Pharmaceutical); $N^1,N^1,N^4,N^4$,2,5-hexamethyl-1,4-benzenediamine (CAS no.: 858341-35-2; provider: Chemieliva Pharmaceutical); $N^1,N^1,N^4,N^4$-tetrakis(1-methylethyl)-1,4-benzenediamine (CAS no.: 6864-03-5; provider: Chemieliva Pharmaceutical); $N^1,N^1,N^4,N^4$,2,3,5,6-octamethyl-1,4-benzenediamine (CAS no.: 66907-63-9; provider: Chemieliva Pharmaceutical); N,N,3,5-tetramethylbenzenamine (CAS no.: 4913-13-7; provider: ASW MedChem); 3,5-diethyl-N,N-dimethylbenzenamine (CAS no.: 99052-31-0; provider: Milestone Pharmtech); 3,5-bis(1,1-dimethylethyl)-N,N-diethylbenzenamine (CAS no.: 94042-96-3; provider: Chemieliva Pharmaceutical); $N^1,N^1,N^3,N^3$-tetramethyl-1,3-benzenediamine (CAS no.: 22440-93-3; provider: ABClabtory Scientific Co.); $N^1,N^1,N^3,N^3$-tetraethyl-1,3-benzenediamine (CAS no.: 64287-26-9; provider: Chemieliva Pharmaceutical); $N^1,N^1,N^3,N^3$,4-pentamethylbenzene-1,3-diamine (CAS no.: 65198-15-4; provider: Chemieliva Pharmaceutical); $N^1,N^1,N^3,N^3$-tetramethyl-5-propyl-1,3-benzenediamine (CAS no.: 1586869-62-6; provider: Chemieliva Pharmaceutical); N,N-dimethylnaphthalen-1-amine (CAS no.: 86-56-6; provider: Alchem Pharmtech); N-ethyl-N-methyl-naphthalen-1-amine (CAS no.: 83777-94-0; provider: Chemieliva Pharmaceutical); N,N,4-trimethylnaphthalen-1-amine (CAS no.: 4523-52-8; provider: ASW MedChem); N,N,5-trimethylnaphthalen-1-amine (CAS no.: 847449-78-9; provider: Chemieliva Pharmaceutical); N,N,2-trimethylnaphthalen-1-amine (CAS no.: 57585-25-8; provider: Chemieliva Pharmaceutical); N,N-diethylnaphthalen-1-amine (CAS no.: 84-95-7; provider: ASW MedChem); N-isopropyl-N-methylnaphthalen-1-amine (CAS no.: 110014-41-0; provider: Chemieliva Pharmaceutical); N,N,4,5-tetramethylnaphthalen-1-amine (CAS no.: 4619-41-4; provider: Chemieliva Pharmaceutical); N-ethyl-N-isopropylnaphthalen-1-amine (CAS no.: 114326-20-4; provider: Chemieliva Pharmaceutical); N-ethyl-N,2-dimethylnaphthalen-1-amine (CAS no.: 130523-07-8; provider: Chemieliva Pharmaceutical); N,N-bis(1-methylethyl)-naphthalen-1-amine (CAS no.: 4960-24-1; provider: Chemieliva Pharmaceutical); N-(1,1-dimethylethyl)-N-methyl-naphthalen-1-amine (CAS no.: 110014-43-2; provider: Chemieliva Pharmaceutical); $N^1,N^1,N^5,N^5$-tetramethyl-naphthalene-1,5-diamine (CAS no.: 10075-69-1; provider: Chemieliva Pharmaceutical); $N^1,N^1,N^4,N^4$-tetramethyl-naphthalene-1,4-diamine (CAS no.: 13764-14-2; provider: Chemieliva Pharmaceutical); N-(1-ethylpropyl)-N-methyl-naphthalen-1-amine (CAS no.: 110014-42-1; provider: Chemieliva Pharmaceutical); N,2-dimethyl-N-(1-methylethyl)-naphthalen-1-amine (CAS no.: 130523-08-9; provider: Chemieliva Pharmaceutical); $N^1,N^1N^8,N^8$-tetramethyl-naphthalene-1,4-diamine (CAS no.: 20734-58-1; provider: ASW MedChem); N,N-diethyl-2-methyl-naphthalen-1-amine (CAS no.: 21614-05-1; provider: Chemieliva Pharmaceutical); N,N-diethyl-8-methyl-naphthalen-1-amine (CAS no.: 130523-22-7; provider: Chemieliva Pharmaceutical); N-(2,2-dimethylpropyl)-N-methyl-naphthalene-1-amine (CAS no.: 110014-40-9; provider: Chemieliva Pharmaceutical); N-(2,2-dimethylpropyl)-N-ethyl-naphthalene-1-amine (CAS no.: 114326-22-6; provider: Chemieliva Pharmaceutical); N,2-diethyl-N-methyl-naphthalene-1-amine (CAS no.: 130523-10-3; provider: Chemieliva Pharmaceutical); N,N-dibutyl-naphthalene-1-amine (CAS no.: 204126-63-6; provider: Chemieliva Pharmaceutical); N-ethyl-2-methyl-N-(1-methylethyl)-naphthalene-1-amine (CAS no.: 130523-09-0; provider: Chemieliva Pharmaceutical); 2-ethyl-N-methyl-N-(1-methylethyl)-naphthalene-1-amine (CAS no.: 130523-12-5; provider: Chemieliva Pharmaceutical); $N^1$-ethyl-$N^1N^5,N^5$-trimethyl-naphthalene-1,8-diamine (CAS no.: 79687-92-6; provider: Chemieliva Pharmaceutical); N-ethyl-N-(1-ethylpropyl)-naphthalene-1-amine (CAS no.: 114326-21-5; provider: Chemieliva Pharmaceutical); N-ethyl-N-methyl-2-(1-methylethyl)-naphthalene-1-amine (CAS no.: 130523-14-7; provider: Chemieliva Pharmaceutical); 8-butyl-N,N-dimethyl-naphthalene-1-amine (CAS no.: 1469538-06-4; provider: Chemieliva Pharmaceutical); N,N-bis(2-methylpropyl)-naphthalene-1-amine (CAS no.: 109556-56-1; provider: Chemieliva Pharmaceutical); N,N,2-triethyl-naphthalene-1-amine (CAS no.: 130523-11-4; provider: Chemieliva Pharmaceutical); N,2-diethyl-N-(1-methylethyl)-naphthalene-1-amine (CAS no.: 130523-13-6; provider: Chemieliva Pharmaceutical); N-methyl-N,2-bis(1-methylethyl)-naphthalene-1-amine (CAS no.: 130523-16-9; provider: Chemieliva Pharmaceutical); N,N-diethyl-2-(1-methylethyl)-naphthalene-1-amine (CAS no.: 130523-15-8; provider: Chemieliva Pharmaceutical); 2-(1,1-dimethylethyl)-N-ethyl-N-methyl-naphthalene-1-amine (CAS no.: 130523-18-1; provider: Chemieliva Pharmaceutical); $N^1,N^1,N^8,N^8$-tetraethyl-naphthalene-1,8-diamine (CAS no.: 53463-80-2; provider: Chemieliva Pharmaceutical); $N^1,N^1$, $N^5,N^5$-tetraethyl-naphthalene-1,5-diamine (CAS no.: 861347-34-4); $N^1,N^5$-dimethyl-$N^1,N^5$-bis(1-methylethyl)-naphthalene-1,5-diamine (CAS no.: 110971-36-3; provider: Chemieliva Pharmaceutical); N-ethyl-N,2-bis(1-methylethyl)-naphthalene-1-amine (CAS no.: 130523-17-0; provider: Chemieliva Pharmaceutical); 2-(1,1-dimethylethyl)-N-methyl-N-(1-methylethyl)-naphthalene-1-amine (CAS no.: 130523-20-5, provider: Chemieliva Pharmaceutical); 2-(1,1-dimethylethyl)-N,N-diethyl-naphthalene-1-amine (CAS no.: 130523-19-2; provider: Chemieliva Pharmaceutical); 3-butyl-NN-diethyl-naphthalene-1-amine (CAS no.: 398458-74-7, provider: Chemieliva Pharmaceutical); 2-(1,1-dimethylethyl)-N-ethyl-N-(1-methylethyl)-naphthalene-1-amine (CAS no.: 130523-21-6, provider: Chemieliva Pharmaceutical); $N^1$-butyl-$N^1,N^8,N^8$-trimethyl-naphthalene-1,8-diamine (CAS no.: 852630-17-2, provider: Chemieliva Pharmaceutical); $N^1,N^6$-dibutyl-$N^1,N^8$-dimethyl-naphthalene-1,8-diamine (CAS no.: 852630-27-4, provider: Chemieliva Pharmaceutical); N,N-dimethyl-naphthalene-2-amine (CAS no.: 2436-85-3, provider: ASW MedChem); N-ethyl-N-methyl-naphthalene-1-amine (CAS no.: 68172-51-0, provider: Chemieliva Pharmaceutical); N,N,4-trimethyl-naphthalene-2-amine (CAS no.: 4523-53-9, provider: Chemieliva Pharmaceutical); N,N,1-trimethyl-naphthalene-2-amine (CAS no.: 5672-92-4, provider: Chemieliva Pharmaceutical); N,N-diethyl-naphthalene-2-amine (CAS no.: 13672-17-8, provider: Chemieliva Pharmaceutical); N-methyl-N-(1-methylethyl)-naphthalene-2-amine (CAS no.: 110014-44-3, provider: Chemieliva Pharmaceutical); N,N,4,5-tetramethyl-naphthalene-2-amine (CAS no.: 4536-94-1, provider: Chemieliva Pharmaceutical); N-butyl-N-methyl-naphthalene-2-amine (CAS no.: 872801-93-9, provider: Chemieliva Pharmaceutical); N,N-bis(1-methylethyl)-naphthalene-2-amine (CAS no.: 92596-72-0, provider: Chemieliva Pharmaceutical); N,N-dibutyl-naphthalene-2-amine (CAS no.: 97943-52-7, provider: Chemieliva Pharmaceutical); N,N-bis(2-methylpropyl)-naphthalene-2-amine (CAS no.: 109554-95-2, provider: Chemieliva Pharmaceutical); 1-(naphthalen-1-yl)piperidine (CAS no.: 62062-39-9, provider: Chemieliva Pharmaceutical); and N,N-dibutyl-1-methyl-naphthalene-2-amine (CAS no.: 92834-61-2, provider: Chemieliva Pharmaceutical).

The naphthacene derivative of general formula (V) is preferably characterized by a boiling point lower than about 650° C. at 760 mm Hg. Examples of naphthacene derivative of general formula (V), include, but are not limited to: 1,11-diphenyl-naphthacene (CAS no.: 927669-50-9; provider: Advanced Organic Synthesis); 5,12-diphenyl-naphthacene (CAS no.: 27130-32-1; provider: Chemieliva Pharmaceutical Co); 5,6,11,12-tetraphenyl-naphthacene (CAS no.: 517-51-1; provider: Chemieliva Pharmaceutical Co); and 5,12-bis[4-(1,1-dimethylethyl)phenyl]-naphthacene (CAS no.: 478799-46-1; provider: Chemieliva Pharmaceutical Co).

EXAMPLES

The present invention is now described in greater detail with respect to non-limiting examples.

General

The marker 2-ethyl-9,10-dimethoxyanthracene (CAS no, 26708-04-3) (97%) was purchased from Sigma Aldrich and was used without further purification.

I. Apparatus and Analytical Method

Two different, but comparable set-ups were built up: the first one described at item I.a below was used for conducting laser ionization—mass spectrometry measurements and the second one described at item I.b below was used for conducting laser ionization—ion mobility spectrometry measurements. In both set-ups, an optical parametric oscillator (OPO) pumped by a Nd:YAG laser (NT342A-SH, Ekspla) was used for samples ionization.

I.a Description Instrument and Method for Analysis by Laser Ionization—Mass Spectrometry.

The set-up used for conducting the laser ionization—mass spectrometry analysis contains a thermal desorption unit (Thermo desorber TC-13,006 from PAS Technology), an optical parametric oscillator (OPO) pumped by a Nd:YAG laser (NT342A-SH, Ekspla), and a commercial mass spectrometer (LTQ XL™, Thermo Fisher Scientific) equipped with a self-made ion source (*J. Mass Spectrorn.* (2016), 51, 566-577) having two quartz windows transparent to a laser beam. The thermal desorption unit is connected via a metal capillary (stainless steel tubing ⅛" outer diameter×2.0 mm inner diameter, about 60 mm long from Ziemer Chromatographie) to the ion source of the mass spectrometer.

The compositions of petroleum hydrocarbon were analyzed by the following method: 2 μL of the liquid sample were introduced using a syringe (Hamilton, 10 μL) into the thermal desorption unit heated to 250° C. Following vaporization, the gaseous sample was transferred via the metal capillary heated to 200° C. (about 60 mm long) using a $N_2$ flow (600 mL/min) in the ionization chamber heated to 120° C. (about 18 mm long, inner diameter of 20 mm) of the ion source, where the gaseous sample was subjected to laser ionization. The ionized sample was then transferred into the MS spectrometer ($N_2$ flow: 1000 mL/min; V: 50 Volts) and the MS spectrum was measured in relative intensities as a function of mass-to-charge ratio (m/z).

I.b Description Instrument and Method for Analysis by Laser Ionization—Ion Mobility Spectrometry.

The set-up used for conducting the laser ionization—ion mobility spectrometry analysis contains an injector of a commercial gas chromatograph (HP 5890 SII, Hewlett Packard, now: Agilent) used only for sample vaporization, a self-made ion mobility spectrometer (*Anal. Bional. Chem.* 405, 7019) having quartz windows transparent to a laser beam and an optical parametric oscillator (OPO) pumped by a Nd:YAG laser (NT342A-SH, Ekspla). The injector of the gas chromatograph is connected via a capillary (deactivated fused silica capillary, 0.18 mm inner diameter, 400 mm long from Perkin Elmer) to the ion source of the ion mobility spectrometer. The drift tube of the ion mobility spectrometer is 100 mm long and has an inner diameter of 25 mm. The ion currents on the Faraday plate are amplified (1 GV/A amplifier, ISAS Dortmund) and recorded on a USB oscilloscope (Handyscope HS3, 5 MHz, Tiepie Engineering).

The compositions of petroleum hydrocarbon were analyzed by the following method: 2 μL of the liquid sample were introduced using a syringe (Hamilton, 10 μL) into an injector (inlet gas: $N_2$; flow inlet gas: 200 mL/min) heated to 250° C. of the commercial gas chromatograph. Following vaporization, the gaseous sample was transferred using a $N_2$ flow of 15 mL/min via the uncoated metal capillary heated to 200° C. (400 mm long) into the ionization chamber heated to 180° C. (about 18 mm long, inner diameter of 20 mm) of the ion mobility spectrometer, where the gaseous sample was subjected to laser ionization. The ionized sample entered the heated drift tube (150° C.) of the ion mobility spectrometer. Nitrogen (flow: 200 mL/min; drift tube voltage: 4.5 kV) or helium (flow: 200 mL/rain; drift tube voltage: 2.5 kV) was used as drift gas. The ion currents on the Faraday plate were amplified (1 GV/A amplifier, ISAS Dortmund) and recorded on a USB oscilloscope (Handyscope HS3, 5 MHz, Tiepie Engineering).

II. Marking of Petroleum Hydrocarbons

For petroleum hydrocarbon marking, a concentrate of 2-ethyl-9,10-dimethoxyanthracene in hexane was prepared to a concentration of 5 mmol/L and added to diesel, gasoline or hexane to yield marked diesel samples (2-ethyl-9,10-dimethoxyanthracene concentration: 1 µM, 2.5 µM, 5 µM, 10 µM, 20 µM, 25 µM, 50 µM, 100 µM, 200 µM, 500 µM, 1 mM), marked gasoline samples (2-ethyl-9,10-dimethoxyanthracene concentration: 5 µM, 10 µM, 20 µM, 50 µM, 100 µM, 200 µM, 500 µM, 1 mM) and marked hexane samples (2-ethyl-9,10-dimethoxyanthracene concentration: 50 µM, 100 µM, 200 µM, 500 µM, 1 mM).

III. Results

Figure 2A:
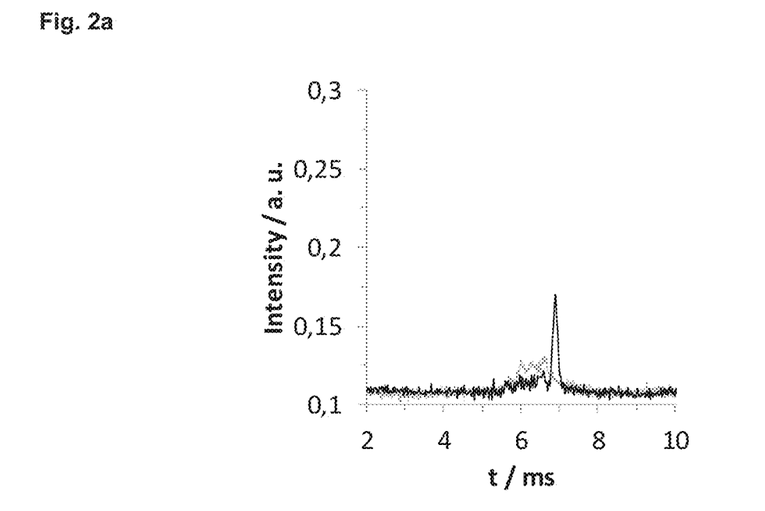
FIG. 2a illustrates the superimposed ion mobility spectra of a composition of diesel containing the chemical marker 2-ethyl-9,10-dimethoxy-anthracene (black colored spectrum) and of the corresponding unmarked diesel (grey colored spectrum) obtained by laser ionization at 355 nm coupled with ion mobility spectrometry. The chemical marker 2-ethyl-9,10-dimethoxy-anthracene is characterized by a drift time of about 7.0 ms.
Figure 2B:
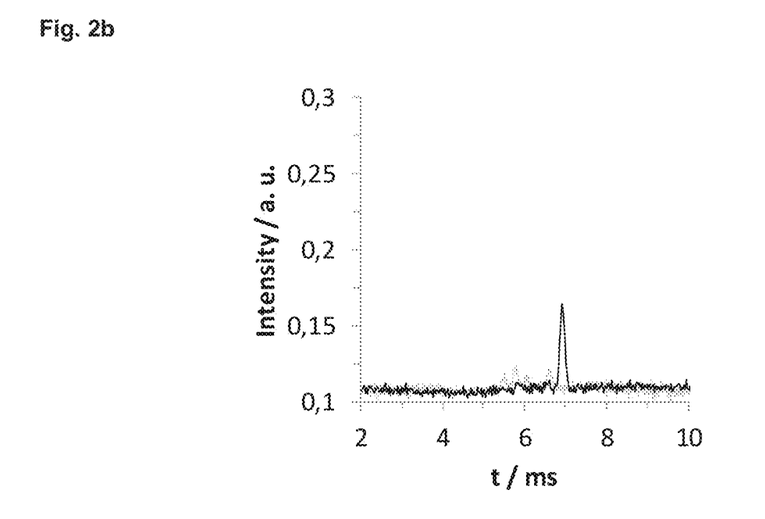
FIG. 2b illustrates the superimposed ion mobility spectra of a composition of gasoline containing the chemical marker 2-ethyl-9,10-dimethoxy-anthracene (black colored spectrum) and of the corresponding unmarked gasoline (grey colored spectrum) obtained by laser ionization at 355 nm coupled with ion mobility spectrometry. The chemical marker 2-ethyl-9,10-dimethoxy-anthracene is characterized by a drift time of about 7.0 ms.
Figure 2C:
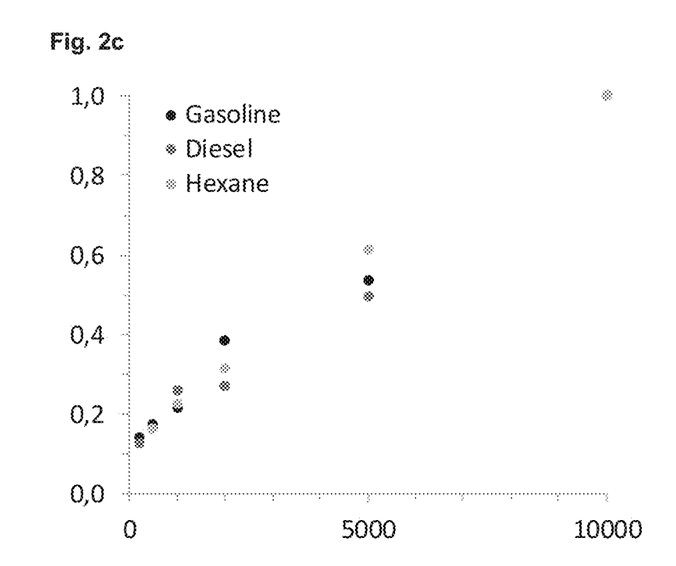
FIG. 2c illustrates the variation of the intensity of the drift time peak corresponding to the chemical marker 2-ethyl-9,10-dimethoxy-anthracene with the concentration of the chemical marker in a composition of gasoline, a composition of diesel and a composition of hexane, respectively. The compositions containing the chemical marker were analyzed by laser ionization at 355 nm coupled with ion mobility spectrometry.

Samples of marked diesel, marked gasoline and marked hexane were analysed by laser ionization at different wavelengths—mass spectrometry using the method m described at item I.a conducted on the instrument described at item I.a (see for e.g. FIG. 1a-1d), as well as by laser ionization at 355 nm—ion mobility spectrometry using the method described at item I.b conducted on the instrument described at item I.b (see for e.g. FIG. 2a-2c).

FIG. 1a illustrates the mass spectrum of a composition of diesel containing the chemical marker 2-ethyl-9,10-dimethoxy-anthracene obtained by laser ionization at 308 nm (pulse energy density of 0.30 mJ/mm$^2$) coupled with mass spectrometry. To minimize the contamination of the mass spectrometer, the composition of diesel according to the present invention was diluted in hexane (1:100, v/v) prior to the analysis. Following dilution, the concentration of the chemical marker in the sample was of 250 nM. The peak corresponding to the ion (M$^+$) of the chemical marker 2-ethyl-9,10-dimethoxy-anthracene (m/z of 266) is indicated by a "*". As attested by the mass spectrometry spectrum, the chemical marker 2-ethyl-9,10-dimethoxy-anthracene has the advantage of being selectively ionized by laser ionization at 308 nm (pulse energy density of 0.30 mJ/mm$^2$) exhibiting the highest intensity in the mass spectrometry spectrum. Thus, even when used in low concentration for marking a petroleum hydrocarbon, the chemical marker 2-ethyl-9,10-dimethoxy-anthracene is easily detectable and identifiable.

FIG. 1b illustrates the mass spectrum of a composition of diesel containing the chemical marker 2-ethyl-9,10-dimethoxy-anthracene obtained by laser ionization at 337 nm (pulse energy density of 0.05 mJ/mm$^2$) coupled with mass spectrometry. To minimize the contamination of the mass spectrometer, the composition of diesel according to the present invention was diluted in hexane (1:100, v/v) prior to the analysis. Following dilution, the concentration of the chemical marker in the sample was of 250 nM. The peak corresponding to the ion (M$^+$) of the chemical marker 2-ethyl-9,10-dimethoxy-anthracene (m/z of 266) is indicated by a "*". As attested by the mass spectrometry spectrum, the chemical marker 2-ethyl-9,10-dimethoxy-anthracene has the advantage of being selectively ionized by laser ionization at 337 nm (pulse energy density of 0.05 mJ/mm$^2$) exhibiting the highest intensity in the mass spectrometry spectrum. Thus, even when used in low concentration for marking a petroleum hydrocarbon, chemical marker 2-ethyl-9,10-dimethoxy-anthracene is easily detectable and identifiable.

FIG. 1c illustrates the mass spectrum of a composition of diesel containing the chemical marker 2-ethyl-9,10-dimethoxy-anthracene obtained by laser ionization at 355 nm (pulse energy density of 0.63 mJ/mm$^2$) coupled with mass spectrometry, To minimize the contamination of the mass spectrometer, the composition of diesel according to the present invention was diluted in hexane (1:100, v/v) prior to the analysis. Following dilution, the concentration of the chemical marker in the sample was of 250 nM. The peak corresponding to the ion (M$^+$) of the chemical marker 2-ethyl-9,10-dimethoxy-anthracene (m/z of 266) is indicated by a "*" As attested by the mass spectrometry spectrum, the chemical marker 2-ethyl-9,10-dimethoxy-anthracene has the advantage of being selectively ionized by laser ionization at 355 nm (pulse energy density of 0.63 mJ/mm$^2$) exhibiting the highest intensity in the mass spectrometry spectrum. Thus, even when used in low concentration for marking a petroleum hydrocarbon, the chemical marker 2-ethyl-9,10-dimethoxy-anthracene is easily detectable and identifiable.

FIG. 1d illustrates the variation of the intensity of the peak corresponding to the molecular ion (M$^+$) of the chemical marker 2-ethyl-9,10-dimethoxy-anthracene with the concentration of the chemical marker in a composition of gasoline, a composition of diesel and a composition of hexane, respectively. The compositions containing the chemical marker 2-ethyl-9,10-dimethoxy-anthracene at different concentrations were analyzed by laser ionization at 355 nm (pulse energy density of 0.63 mJ/mm$^2$) coupled with mass spectrometry. To minimize the contamination of the mass spectrometer, the compositions of diesel according to the present invention were diluted in hexane (1:100, v/v) prior to the analysis. As attested by FIG. 1d, the chemical marker 2-ethyl-9,10-dimethoxy-anthracene is easily detectable, identifiable and quantifiable even at low concentration of 1 µM by laser ionization at 355 nm (pulse energy density of 0.63 mJ/mm$^2$) coupled with mass spectrometry.

FIG. 2a illustrates the superimposed ion mobility spectra of a composition of diesel containing the chemical marker 2-ethyl-9,10-dimethoxy-anthracene (black colored spectrum) and of the corresponding unmarked diesel (grey colored spectrum) obtained by laser ionization at 355 nm (pulse energy density of 0.63 mJ/mm$^2$) coupled with ion mobility spectrometry (drift gas: helium; flow: 200 ml/min; drift tube voltage: 2.5 kV). Both the composition of diesel containing the chemical marker and the unmarked diesel were diluted in hexane (1:100, v/v) prior to analysis to minimize the contamination of the spectrometer. Following dilution, the concentration of the chemical marker in the sample was of 10 µM. The chemical marker 2-ethyl-9,10-dimethoxy-anthracene is characterized by a drift time of about 7.0 ms. As shown in FIG. 2a, as diesel generates a negligible background noise when subjected to laser ionization at 355 nm pulse energy density of 0.63 mJ/mm$^2$) coupled with ion mobility spectrometry, the chemical marker 2-ethyl-9,10-dimethoxy-anthracene is easily detectable and identifiable even at low concentration of 1 mM in a composition of diesel.

FIG. 2b illustrates the superimposed ion mobility spectra of a composition of gasoline containing the chemical marker 2-ethyl-9,10-dimethoxy-anthracene (black colored spectrum) and of the corresponding unmarked gasoline (grey colored spectrum) obtained by laser ionization at 355 nm (pulse energy density of 0.63 mJ/mm$^2$) coupled with ion mobility spectrometry (drift gas: helium; flow: 200 ml/min; drift tube voltage: 2.5 kV). Both the composition of gasoline containing the chemical marker and the unmarked gasoline were diluted in hexane (1:100; v/v) prior to analysis to minimize the contamination of the spectrometer. Following dilution, the concentration of the chemical marker in the sample was of 10 µM. The chemical marker 2-ethyl-9,10- dimethoxy-anthracene is characterized by a drift time of about 7.0 ms. As attested by FIG. 2b, gasoline generates a negligible background noise when subjected to laser ionization at 355 nm (pulse energy density of 0.63 mJ/mm$^2$) coupled with ion mobility spectrometry, and consequently, the chemical marker 2-ethyl-9,10-dimethoxy-anthracene can be easily detected and identified even at low concentration of 1 mM in a composition of gasoline.

FIG. 2c illustrates the variation of the intensity of the drift time peak corresponding to the chemical marker 2-ethyl-9, 10-dimethoxy-anthracene with the concentration of the chemical marker in a composition of gasoline, a composition of diesel and a composition of hexane, respectively. The compositions containing the chemical marker were analyzed by laser ionization at 355 nm (pulse energy density of 0.63 mJ/mm$^2$) coupled with ion mobility spectrometry (drift gas: helium; flow: 200 ml/min; drift tube voltage: 2.5 kV). To minimize the contamination of the spectrometer, the compositions of diesel and gasoline according to the present invention were diluted in hexane to 1:100 (v/v) prior to the analysis. The perfect linearity and the overlapping of the three calibration curves prove that chemical marker 2-ethyl-9,10-dimethoxy-anthracene is suitable for marking a variety of petroleum hydrocarbons, including diesel and gasoline. The chemical marker 2-ethyl-9,10-dimethoxy-anthracene has the advantage of being selectively ionized upon laser ionization at 355 nm (pulse energy density of 0.63 mJ/mm$^2$), Thus, even low concentrations of the chemical marker are detectable, identifiable and quantifiable in complex petroleum hydrocarbons by combining laser selective ionization at 355 nm with ion mobility spectrometry.

The invention claimed is:

1. A composition of a petroleum hydrocarbon comprising:
   a petroleum hydrocarbon;
   at least one chemical marker of general formula (I) uniformly mixed with the petroleum hydrocarbon (I)

wherein two of the residues $R^1$-$R^{10}$ are independently selected from $C_1$-$C_4$-alkoxy, and eight of the residues $R^1$-$R^{10}$ are independently selected from the group consisting of hydrogen and $C_1$-$C_4$-alkyl; and a diphenyl-polyene derivative of general formula (IV)

(IV)

wherein $R^{13}$-$R^{22}$ are independently selected from the group consisting of hydrogen and $C_1$-$C_4$ alkyl; the residue -L- represents —$CR^a$=$CR^b$—, wherein $R^a$ and $R^b$ are independently selected from the group consisting of hydrogen and methyl; and n is an integer between 2 and 6.

2. The composition according to claim 1, wherein the at least one chemical marker of general formula (I) has a concentration of at least 1 μM.

3. The composition according to claim 1, wherein the at least one chemical marker is of general formula (II)

(II)

wherein the residues $R^1$-$R^4$ and $R^6$-$R^9$ are independently of each other selected from the group consisting of hydrogen and $C_1$-$C_4$-alkyl, and the residues $R^{11}$ and $R^{12}$ are independently of each other selected from $C_1$-$C_4$-alkyl.

4. The composition according to claim 3, wherein the residues $R^6$-$R^9$ represent hydrogen.

5. The composition according to claim 3, wherein the residues $R^1$-$R^4$ and $R^6$-$R^9$ are independently of each other selected from $C_1$-$C_4$-alkyl.

6. The composition according to claim 3, wherein the residues $R^1$-$R^4$ and $R^6$-$R^9$ represent hydrogen.

7. The composition according to claim 1, wherein the at least one chemical marker is of general formula (III)

(III)

wherein the residue $R^2$ is selected from the group consisting of hydrogen and $C_1$-$C_4$-alkyl, and the residues $R^{11}$ and $R^{12}$ are independently of each other selected from $C_1$-$C_4$-alkyl.

8. The composition according to claim 3, wherein the residues $R^{11}$ and $R^{12}$ are the same.

9. The composition according to claim 1, wherein the petroleum hydrocarbon is selected from crude oil, lubricating oil, brake fluid, gasoline, diesel fuel, kerosene, jet fuel, heating oil and heavy fuel oil.

10. The composition according to claim 1, further comprising:
    an aromatic compound substituted by one or more N,N-disubstituted amino groups, wherein the substituents of the one or more N,N-disubstituted amino groups are independently of each other selected from $C_1$-$C_6$-alkyl; and a naphthacene derivative of general formula (V)

(I)

wherein $R^{23}$-$R^{34}$ are independently selected from the group consisting of hydrogen, $C_1$-$C_4$-alkyl and phenyl optionally substituted by one or more groups selected from $C_1$-$C_4$-alkyl, and at least two of $R^{23}$-$R^{34}$ represent a phenyl optionally substituted by one or more groups selected from $C_1$-$C_4$-alkyl.

* * * * *